United States Patent [19]

Talley

[11] Patent Number: 4,551,563

[45] Date of Patent: Nov. 5, 1985

[54] METHOD FOR MAKING POLYMETHYLATED PHENOLS

[75] Inventor: John J. Talley, Clifton Park, N.Y.

[73] Assignee: General Electric Company, Schenectady, N.Y.

[21] Appl. No.: 613,546

[22] Filed: May 24, 1984

[51] Int. Cl.[4] .................. C07C 37/16; C07C 39/07
[52] U.S. Cl. ................................. 568/804; 568/716
[58] Field of Search ........................ 568/804, 716

[56] References Cited

U.S. PATENT DOCUMENTS

| | | | |
|---|---|---|---|
| 2,701,264 | 2/1955 | Deahl et al. | 568/716 |
| 3,833,673 | 9/1974 | Brannock | 568/716 |
| 3,859,365 | 1/1975 | Young | 568/716 |
| 4,086,282 | 4/1978 | Wattimena | 568/804 |

FOREIGN PATENT DOCUMENTS

| | | | |
|---|---|---|---|
| 1181437 | 2/1970 | United Kingdom | 568/716 |
| 1197802 | 7/1970 | United Kingdom | 568/716 |

Primary Examiner—Werren B. Lone
Attorney, Agent, or Firm—William A. Teoli; James C. Davis, Jr.; James Magee, Jr.

[57] ABSTRACT

A method is provided for making polymethylated phenols, such as 2,3,5-trimethylphenol and 2,3,5,6-tetramethylphenol from a mixture of isophorone and methanol. Catalytic demethanation of isophorone and methanation of the resulting product is achieved by contacting the mixture of isophorone and methanol with the calcination residue of a mixture of magnesium carbonate and/or magnesium hydroxide and a manganese compound at elevated temperatures.

4 Claims, No Drawings

METHOD FOR MAKING POLYMETHYLATED PHENOLS

BACKGROUND OF THE INVENTION

Prior to the present invention, 2,3,5-trimethylphenol was prepared from a mixture of isophorone and methanol by contacting the mixture with an alumina, chromium oxide and potassium oxide catalyst at a temperature of 630° C. It would be desirable to synthesize polymethylated phenols from a mixture of isophorone and methanol at a substantially reduced temperature.

The present invention is based on the discovery that polymethylated phenols having the formula

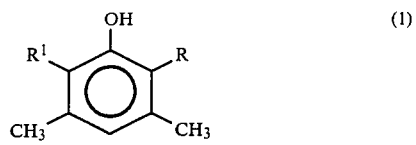

can be made by contacting a mixture of isophorone and methanol with the calcination residue of a mixture of magnesium carbonate and/or magnesium hydroxide and manganese hydroxide at a temperature in the range of from about 400° C. to 550° C., where R and $R^1$ are members selected from hydrogen and methyl.

STATEMENT OF THE INVENTION

There is provided by the present invention, a method for making polymethylated phenols of formula (1) from a mixture of isophorone and methanol, comprising effecting contact between an isophorone and methanol mixture having from 0.5 to 5 moles of methanol per mole of isophorone, and the calcination residue of a mixture of magnesium carbonate and/or magnesium hydroxide and manganese hydroxide at a temperature in the range of from about 400° to about 550° C., where the mixture of isophorone and methanol is passed over the calcination residue at a rate sufficient to maintain a liquid hourly space velocity (LHSV) having a value of from about 0.1 to 3 where $$LHSV = \frac{\text{volume of feed passed over calcination residue per hour}}{\text{volume of a dry mixture of magnesium carbonate and/or magnesium hydroxide and manganese hydroxide prior to calcination}}$$

Some of the methylated phenols which can be made in accordance with the practice of the present invention are 3,5-xylenol, 2,3,5-trimethylphenol and 2,3,5,6-tetramethylphenol.

The catalyst of the present invention is in the form of a calcination residue of a mixture of magnesium carbonate and/or magnesium hydroxide and a manganese compound. The catalyst can be made by combining magnesium carbonate and/or magnesium hydroxide and manganese hydroxide with subsequent calcination at elevated temperatures to form the active catalyst composite. Manganese hydroxide can be precipitated in the presence of a basic magnesium carbonate, that is $x$MgCO$_3$.Mg(OH)$_2$.XH$_2$O, where x can be from 3 to about 5. The manganese hydroxide can be generated from a water soluble salt of manganese, for example manganese nitrate, which forms a precipitate of manganese hydroxide in the presence of a basic magnesium carbonate. The resulting mixture of basic magnesium carbonate and manganese hydroxide, which can be present at from 1 to 10% by weight of the uncalcined mixture, can be shaped into convenient catalyst pellets in paste form by extrusion, molding or other conventional shaping techniques. Calcination of the pellets can be effected at temperatures of from 300°–500° C. or higher during the demethanation of the isophorone and the resulting methanation of the resulting product. If desired, water soluble synthetic resins, such as polyphenylene oxide, polyvinylalcohol polymers, acrylics, sodium carboxymethyl cellulose and the like, can be used as shaping aids in the formation of wet pellets of the magnesium-manganese catalyst composite. A preferred polyphenylene oxide is poly-(2,6-dimethyl-1,4-phenylene)-oxide, hereinafter referred to as polyphenylene oxide.

In the practice of the invention, the mixture of isophorone and methanol as previously defined can be passed over the calcination residue of the mixture of magnesium carbonate and/or magnesium hydroxide and a manganese compound, referred to hereinafter as "calcination residue" at a temperature in the range as previously defined. Preferably, the calcination residue is formed prior to contact with the mixture of isophorone and methanol. A convenient procedure, for example, is activating the magnesium carbonate and/or magnesium hydroxide mixture and a manganese compound by heating the aforementioned ingredients under a neutral atmosphere such as a nitrogen atmosphere at temperatures in the range of from 400° C. to 600° C. over a period of from 1 to 10 hours. Experience has shown that depending upon the ratio of methanol to isophorone utilized in the reaction mixture, the formation of a particulated polymethylated phenol such as 2,3,5,6-tetramethylphenol or 2,3,6-trimethylphenol can be favored. For example 2,3,5-trimethylphenol an important starting material for the preparation of 2,3,5-trimethyl-hydroquinone can be favored if a ratio of isophorone to methanol of 1 or less is utilized. Alternatively, a ratio of isophorone to methanol greater than unity has been found to favor the formation of 2,3,5,6-tetramethylphenol.

An important consideration of the present invention is maintaining the LHSV in the range of from 0.1 to 3 under continuous or batch conditions during the formation of the desired polymethylated phenol.

It has been found that the pyrolysis of the methylated cyclohexenone can be expressed on a weight basis as follows:

$$WHSV = \frac{\text{weight of the feed passed over the catalyst in an hour}}{\text{weight of the uncalcined catalyst}}$$

In converting LHSV to WHSV, a density of about 0.8 for the uncalcined magnesium carbonate mixture as previously defined, or uncalcined catalyst can be used. In addition, the uncalcined catalyst can experience a weight loss of about 30 to 70% based on the weight of the original uncalcined mixture.

Recovery of the polymethylated phenol can be readily achieved as a bottoms product when utilizing a reactor in the form of a distillate column. Distillation of the resulting polymethylated phenol reaction mixture under reduced pressure will provide for the recovery of the specific polymethylated phenol, such as 3,5-xylenol 2,3,5-trimethylphenol, and 2,3,5,6-tetramethylphenol. Recovery of specific polymethylated phenols also can be achieved by crystallization, procedures using an organic solvent such as hexane and temperatures of 0° to 25° C.

The following examples are given by way of illustration and not by way of limitation. All parts are by weight unless otherwise indicated.

EXAMPLE 1

A slurry of 518.9 grams of "basic" $MgCO_3$ in 2000 ml of distilled water was combined with 40.0 grams of $Mn(NO_3)_2$, diluted to 500 ml with distilled water over approximately a 4-minute time period. 10.8 grams of a 50% caustic NaOH solution diluted to 500 ml with distilled water was added to the resulting admixture over approximately 4 minutes, followed by stirring for one hour at room temperature. The slurry was vacuum filtered, washed with 1500 ml of distilled water, resuspended by homogenizing in water and vacuum filtered again. The "resuspension" procedure was repeated four times for a total of five resuspensions and five vacuum filtrations. The filtrate was dried overnight under vacuum in a 103° C. oven and ground to a fine powder. The powder was blended with sufficient polyphenylene oxide to provide 90 parts by weight of "basic" $MgCo_3$ co-precipitated with $Mn(OH)_2$ and 10 parts by weight of polyphenylene oxide. The 90:10 powder blend was precompressed in a tableting press, ground and sifted through a #25 screen, and tableted to form $3/16'' \times \frac{1}{8}''$ pellets.

A series of polymethylated phenols were prepared by using an electrically heated vertical quartz tube (30 cm×25 mm) filled by the following materials: 5 cm of quartz chips, 20 cm of the above magnesium carbonate catalyst, and 5 cm of quartz chips. The reaction contents were heated to a temperature of 500° C. for a period of 2-4 hours to activate the catalyst in a steam of dry nitrogen. A mixture of isophorone in methanol was then passed over the catalyst in a steam of nitrogen. The resulting reaction mixture was then analyzed by gas liquid chromatography. The identity of the products was further confirmed by comparison with authentic samples, GC, IR, NMR and their respective melting points. In an initial reaction a mixture of two moles of isophorone per mole of methanol was passed over the calcination residue at 500° C. at an LHSV of 0.5. Recovery of the resulting product provided a polymethylated phenol mixture having the following composition.

TABLE I

| Weight percent | Component |
|---|---|
| 8.6 | Isophorone |
| 19.1 | 3,5-Dimethylphenol |
| 8.6 | 2,3,5-Trimethylphenol |
| 39 | 2,3,5,6-Tetramethylphenol |

The above results show that the 2,3,5,6-tetramethylphenol is favored utilizing a 2:1 isophorone/methanol mixture at a LHSV of 0.5.

The crude product was diluted with ether and then extracted with three portions of 10% sodium hydroxide solution. Concentration of the ethereal phase resulted in the isolation of isophorone (recovered starting material). The sodium hydroxide solution was acidified to pH=1 with concentrated hydrochloric acid and the acidic solution extracted with three portions of ether. The ethereal solution was dried and concentrated to provided a mixture of 3,5-xylenol, 2,3,5-trimethylphenol and 2,3,5,6-tetramethylphenol. The mixture of methylated phenols was further purified by medium pressure liquid chromatography on silica gel using mixtures of hexane and ethylacetate as eluant. The order of elution from the column was 2,3,5,6-tetramethylphenol, 2,3,5-trimethylphenol, and finally 3,5-xylenol. The 2,3,5,6-tetramethylphenol had a melting point of 109° C., 2,3,5-trimethylphenol had a melting point of 94° C., and the 3,5-dimethylphenol had a melting point of 65° C.

EXAMPLE 2

The procedure of Example 1 was repeated, except that a mixture of 1.25 moles of isophorone per mole of methanol was used and the LHSV was 0.5. The following results were obtained:

TABLE II

| Weight percent | Component |
|---|---|
| 5.7 | Isophorone |
| 17.8 | 3,5-Xylenol |
| 29.3 | 2,3,5-Trimethylphenol |
| 38.6 | 2,3,5,6-Tetramethylphenol |

EXAMPLE 3

The procedure of Example 1 was repeated, except that a mixture of isophorone to methanol was used having equal molar amounts of isophorone and methanol and the mixture was introduced at a rate sufficient to produce an LHSV of 0.5. There was obtained a polymethylated phenol mixture having the following composition:

TABLE III

| Weight percent | Component |
|---|---|
| 46.8 | Isophorone |
| 24.7 | 3,5-Xylenol |
| 18.8 | 2,3,5-Trimethylphenol |
| 6.4 | 2,3,5,6-Tetramethylphenol |

The above procedure was repeated, except that the isophorone to methanol ratio was reduced to 0.63. There was obtained a mixture of 40.5% isophorone, 17.8% 3,5-xylenol, 16.1% 2,3,5-trimethylphenol and 8% of 2,3,5,6-tetramethylphenol.

The above results show that a significant reduction in the methylation of the resulting methylated phenol is obtained when the ratio of the isophorone/methanol is reduced to unity or below.

Although the above results are directed to only a few of the very many variables which can be used in the practice of the present invention, it should be understood that the present invention is directed to a much broader variety of calcination residues and reaction products which can obtained as the result of the use of such calcination residue with a mixture of methanol and isophorone at elevated temperatures.

What I claim as new and desire to secure by Letters Patent of the United States is:

1. A method for making polymethylated phenols of the formula

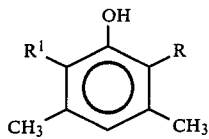 (1)

from a mixture of isophorone and methanol, comprising effecting contact between an isophorone and methanol mixture having from 0.5 to 5 moles of methanol per mole of isophorone, and the calcination residue of a mixture of magnesium carbonate and/or magnesium hydroxide and manganese hydroxide at a temperature in the range of from 400° to 600° C., where the mixture of isophorone and methanol is passed over the calcination residue at a rate sufficient to maintain a liquid hourly space velocity (LHSV) having a value of from about 0.1 to 3 where $$LHSV = \frac{\text{volume of feed passed over calcination residue per hour}}{\text{volume of a dry mixture of magnesium carbonate and/or magnesium hydroxide and manganese hydroxide prior to calcination}}$$ where R and $R^1$ are members selected from hydrogen and methyl 2. The method of claim 1, where the polymethylated phenol is 2,3,5-trimethylphenol.
3. The method of claim 1, where the polymethylated phenol is 2,3,5,6-tetramethylphenol.
4. The method of claim 1, where the polymethylated phenol is 3,5-xylenol-2,3,5-trimethylphenol.

* * * * *